(12) United States Patent
McDonell et al.

(10) Patent No.: US 10,070,990 B2
(45) Date of Patent: Sep. 11, 2018

(54) OPTIMIZED PNEUMATIC DRIVE LINES

(75) Inventors: Brian W. McDonell, Irvine, CA (US); Filip Finodeyev, Laguna Niguel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 56 days.

(21) Appl. No.: 13/314,625

(22) Filed: Dec. 8, 2011

(65) Prior Publication Data

US 2013/0150875 A1   Jun. 13, 2013

(51) Int. Cl.
| | |
|---|---|
| *A61F 9/007* | (2006.01) |
| *A61B 17/32* | (2006.01) |
| *A61M 25/00* | (2006.01) |
| *A61B 17/00* | (2006.01) |

(52) U.S. Cl.
CPC ...... *A61F 9/00763* (2013.01); *A61F 9/00736* (2013.01); *A61B 2017/00544* (2013.01); *A61F 9/007* (2013.01); *A61M 25/0054* (2013.01)

(58) Field of Classification Search
USPC .................................................. 604/23–45
See application file for complete search history.

(56) References Cited

U.S. PATENT DOCUMENTS

| | | | |
|---|---|---|---|
| 812,162 A | 2/1906 | Bemis | |
| 1,993,883 A * | 3/1935 | Heddon | B21B 21/00 138/177 |
| 2,707,389 A | 5/1955 | Fortier | |
| 2,986,169 A * | 5/1961 | McCormick | B29D 23/18 138/109 |
| 3,018,799 A * | 1/1962 | Hartzell et al. | 138/26 |
| 3,084,674 A | 4/1963 | Watson | |
| 3,477,665 A | 11/1969 | Legrand | |
| 3,690,067 A * | 9/1972 | Goss et al. | 451/91 |
| 3,703,139 A | 11/1972 | Furlong | |
| 3,815,604 A * | 6/1974 | O'Malley et al. | 604/22 |
| 3,854,382 A | 12/1974 | Walters | |
| 3,867,934 A | 2/1975 | Ollivier | |
| 3,884,238 A | 5/1975 | O'Malley | |
| 4,077,567 A | 3/1978 | Ginn et al. | |

(Continued)

FOREIGN PATENT DOCUMENTS

| | | |
|---|---|---|
| CN | 1954789 | 5/2007 |
| CN | 101044943 | 4/2009 |

(Continued)

OTHER PUBLICATIONS

Cen-Tec Systems Inc., There is something different, Central Vac Professional, Feb. 2010.*

(Continued)

*Primary Examiner* — Lynsey Eiseman
*Assistant Examiner* — Manolis Pahakis

(57) ABSTRACT

In one exemplary aspect, the present disclosure is directed to a system. The system includes a pneumatic surgical instrument and a surgical console operable to provide compressed gas to the pneumatic surgical instrument. Additionally, the system includes a pneumatic drive line coupling the pneumatic surgical instrument to the surgical console. The pneumatic drive line has an internal bore configured to deliver the compressed gas to the pneumatic surgical instrument. The internal bore has a non-uniform cross-section along a length of the pneumatic drive line.

6 Claims, 7 Drawing Sheets

(56) References Cited

U.S. PATENT DOCUMENTS

| | | | |
|---|---|---|---|
| 4,086,804 A | 5/1978 | Ruby | |
| 4,164,167 A | 8/1979 | Imai et al. | |
| 4,314,560 A * | 2/1982 | Helfgott et al. | 606/171 |
| 4,323,064 A | 4/1982 | Hoenig et al. | |
| 4,331,130 A | 5/1982 | Lewicky | |
| 4,335,867 A | 6/1982 | Bihlmaier | |
| 4,344,144 A | 8/1982 | Damico et al. | |
| 4,418,596 A * | 12/1983 | Garrocho | 83/98 |
| 4,449,550 A | 5/1984 | Ranalli | |
| 4,471,728 A | 9/1984 | Borst et al. | |
| 4,476,532 A | 10/1984 | Akiyama et al. | |
| 4,563,180 A * | 1/1986 | Jervis | A61M 25/0054 |
| | | | 604/523 |
| 4,577,629 A * | 3/1986 | Martinez | 606/171 |
| 4,590,935 A | 5/1986 | Ranalli | |
| 4,622,503 A | 11/1986 | Sundblom et al. | |
| 4,623,327 A * | 11/1986 | Mahurkar | A61M 5/1582 |
| | | | 604/44 |
| 4,629,218 A * | 12/1986 | Dubois | 285/148.22 |
| 4,650,460 A | 3/1987 | Roizenblatt | |
| 4,650,462 A | 3/1987 | DeSatnick et al. | |
| 4,675,004 A * | 6/1987 | Hadford | A61M 5/1582 |
| | | | 604/272 |
| 4,696,298 A | 9/1987 | Higgins et al. | |
| 4,706,687 A | 11/1987 | Rogers | |
| 4,747,820 A * | 5/1988 | Hornlein et al. | 604/22 |
| 4,757,814 A | 7/1988 | Wang et al. | |
| 4,770,654 A | 9/1988 | Rogers et al. | |
| 4,775,371 A * | 10/1988 | Mueller, Jr. | A61M 25/0045 |
| | | | 604/103 |
| 4,790,816 A | 12/1988 | Sundblom et al. | |
| 4,810,242 A | 3/1989 | Sundblom et al. | |
| 4,840,111 A | 6/1989 | Garnjost | |
| 4,909,249 A | 3/1990 | Akkas et al. | |
| 4,909,782 A | 3/1990 | Semm et al. | |
| 4,933,843 A | 6/1990 | Scheller et al. | |
| 4,940,468 A | 7/1990 | Petillo | |
| 4,986,827 A | 1/1991 | Akkas et al. | |
| 5,019,035 A | 5/1991 | Missirlian et al. | |
| 5,019,037 A * | 5/1991 | Wang | A61F 9/00727 |
| | | | 604/121 |
| 5,020,315 A | 6/1991 | Leachman, Jr. et al. | |
| 5,020,535 A | 6/1991 | Parker et al. | |
| 5,020,825 A | 6/1991 | Lizell | |
| 5,024,652 A | 6/1991 | Dumenek et al. | |
| 5,047,008 A | 9/1991 | de Juan, Jr. et al. | |
| 5,059,204 A | 10/1991 | Lawson et al. | |
| 5,092,178 A | 3/1992 | Vanderlaan | |
| 5,099,648 A * | 3/1992 | Angle | 60/726 |
| 5,106,364 A | 4/1992 | Hayafuji et al. | |
| 5,108,400 A | 4/1992 | Appel et al. | |
| 5,154,207 A | 10/1992 | Bolt | |
| 5,259,842 A * | 11/1993 | Plechinger et al. | 604/152 |
| 5,275,607 A | 1/1994 | Lo et al. | |
| 5,314,295 A | 5/1994 | Lukkari et al. | |
| 5,352,194 A | 10/1994 | Greco et al. | |
| 5,364,374 A * | 11/1994 | Morrison | A61F 9/00781 |
| | | | 604/239 |
| 5,380,280 A | 1/1995 | Peterson | |
| 5,403,276 A | 4/1995 | Schechter et al. | |
| 5,417,246 A | 5/1995 | Perkins et al. | |
| 5,429,601 A * | 7/1995 | Conley et al. | 604/65 |
| 5,437,241 A | 8/1995 | Rosenberg et al. | |
| 5,445,773 A | 8/1995 | Arai | |
| 5,474,532 A | 12/1995 | Steppe | |
| 5,485,887 A | 1/1996 | Mandanis | |
| 5,487,725 A * | 1/1996 | Peyman | 604/22 |
| 5,505,210 A | 4/1996 | Clement | |
| 5,520,668 A | 5/1996 | Greff et al. | |
| 5,526,822 A | 6/1996 | Burbank et al. | |
| 5,533,878 A * | 7/1996 | Iwata | F04B 43/1269 |
| | | | 417/477.3 |
| 5,549,139 A | 8/1996 | Perkins et al. | |
| 5,549,547 A * | 8/1996 | Cohen | A61B 17/3203 |
| | | | 604/30 |
| 5,580,347 A | 12/1996 | Reimels | |
| 5,587,536 A | 12/1996 | Rasmussen | |
| 5,602,449 A | 2/1997 | Krause et al. | |
| 5,622,665 A | 4/1997 | Wang | |
| 5,630,827 A | 5/1997 | Vijfvinkel | |
| 5,669,876 A | 9/1997 | Schechter et al. | |
| 5,669,921 A | 9/1997 | Berman et al. | |
| 5,669,923 A | 9/1997 | Gordon | |
| 5,674,194 A | 10/1997 | Jung et al. | |
| 5,701,795 A | 12/1997 | Freidrichsen | |
| 5,712,460 A | 1/1998 | Carr et al. | |
| 5,733,298 A | 3/1998 | Berman et al. | |
| 5,788,651 A | 8/1998 | Weilandt | |
| 5,791,142 A | 8/1998 | Layne et al. | |
| 5,795,323 A | 8/1998 | Cucin | |
| 5,810,765 A | 9/1998 | Oda | |
| 5,810,858 A | 9/1998 | Berman et al. | |
| 5,829,335 A | 11/1998 | Ewald et al. | |
| 5,836,912 A * | 11/1998 | Kusleika | A61M 25/10 |
| | | | 604/523 |
| 5,843,111 A | 12/1998 | Vijfvinkel | |
| 5,846,257 A | 12/1998 | Hood | |
| 5,857,485 A | 1/1999 | Perkins et al. | |
| 5,944,673 A | 8/1999 | Gregoire et al. | |
| 5,979,494 A * | 11/1999 | Perkins et al. | 137/487.5 |
| 5,980,528 A | 11/1999 | Salys | |
| 5,980,546 A | 11/1999 | Hood | |
| 6,007,497 A | 12/1999 | Huitema | |
| 6,019,733 A | 2/2000 | Farascioni | |
| 6,116,284 A * | 9/2000 | Murray et al. | 138/39 |
| 6,162,187 A | 12/2000 | Buzzard et al. | |
| 6,179,829 B1 | 1/2001 | Bisch et al. | |
| 6,213,971 B1 | 4/2001 | Poole | |
| 6,245,084 B1 | 6/2001 | Mark et al. | |
| 6,280,423 B1 * | 8/2001 | Davey | A61M 25/0021 |
| | | | 604/264 |
| 6,358,263 B2 | 3/2002 | Mark et al. | |
| 6,383,203 B1 * | 5/2002 | Makihara | 606/171 |
| 6,425,883 B1 | 7/2002 | Urich et al. | |
| 6,450,966 B1 | 9/2002 | Hanna | |
| 6,506,176 B1 * | 1/2003 | Mittelstein et al. | 604/22 |
| 6,514,268 B2 | 2/2003 | Finlay et al. | |
| 6,575,264 B2 | 6/2003 | Spadafora | |
| 6,575,990 B1 | 6/2003 | Wang et al. | |
| 6,585,683 B2 | 7/2003 | Sutton et al. | |
| 6,678,584 B2 | 1/2004 | Junk et al. | |
| 6,691,798 B1 | 2/2004 | Lindsay | |
| 6,719,011 B2 | 4/2004 | Cull et al. | |
| 6,730,106 B2 | 5/2004 | Kanda et al. | |
| 6,743,245 B2 | 6/2004 | Lobdell | |
| 6,752,795 B2 | 6/2004 | Cull | |
| 6,758,842 B2 | 7/2004 | Irion et al. | |
| 6,773,445 B2 | 8/2004 | Finlay et al. | |
| 6,817,812 B1 | 11/2004 | Christian | |
| 6,848,323 B2 | 2/2005 | Krouth et al. | |
| 6,892,745 B2 | 5/2005 | Benson | |
| 6,926,658 B2 * | 8/2005 | Farnan | A61M 25/0068 |
| | | | 600/3 |
| 6,954,683 B2 | 10/2005 | Junk et al. | |
| 6,960,182 B2 * | 11/2005 | Moutafis | A61B 17/3203 |
| | | | 604/149 |
| 6,999,853 B2 | 2/2006 | Junk et al. | |
| 7,051,995 B2 | 5/2006 | Tornqvist | |
| 7,083,608 B2 | 8/2006 | Tomita et al. | |
| 7,217,257 B2 | 5/2007 | Cull et al. | |
| 7,252,653 B2 * | 8/2007 | Ueda | A61M 5/329 |
| | | | 604/272 |
| 7,263,877 B2 | 9/2007 | Schaefer et al. | |
| 7,331,950 B2 | 2/2008 | Tidwell et al. | |
| 7,335,217 B2 | 2/2008 | Wang et al. | |
| 7,352,287 B2 | 4/2008 | Rupert | |
| 7,422,035 B2 | 9/2008 | Wu | |
| 7,628,054 B2 | 12/2009 | Hajishah et al. | |
| 7,722,544 B2 | 5/2010 | Williams et al. | |
| 7,775,052 B2 | 8/2010 | Cornwell et al. | |
| 7,883,458 B2 | 2/2011 | Hamel | |

(56) References Cited

U.S. PATENT DOCUMENTS

| | | | |
|---|---|---|---|
| 7,981,974 B2* | 7/2011 | Miller | B01D 67/0006 525/419 |
| 8,157,145 B2 | 4/2012 | Shelton, IV et al. | |
| 8,215,108 B2 | 7/2012 | Hahn et al. | |
| 8,230,877 B2 | 7/2012 | Roberge et al. | |
| 8,568,441 B2 | 10/2013 | McEwen et al. | |
| 2002/0002368 A1 | 1/2002 | Tomita et al. | |
| 2002/0022854 A1 | 2/2002 | Irion et al. | |
| 2002/0049461 A1 | 4/2002 | Kanda et al. | |
| 2002/0128560 A1 | 9/2002 | Urich | |
| 2003/0020036 A1 | 1/2003 | Heun et al. | |
| 2003/0195538 A1 | 10/2003 | Wang et al. | |
| 2003/0208305 A1 | 11/2003 | Junk et al. | |
| 2004/0034333 A1 | 2/2004 | Seese et al. | |
| 2004/0154466 A1 | 8/2004 | Gethmann et al. | |
| 2004/0225293 A1* | 11/2004 | Tidwell et al. | 606/79 |
| 2004/0267157 A1 | 12/2004 | Miller et al. | |
| 2005/0113715 A1 | 5/2005 | Schwindt et al. | |
| 2005/0245909 A1 | 11/2005 | McCary et al. | |
| 2005/0251228 A1 | 11/2005 | Hamel | |
| 2005/0256445 A1 | 11/2005 | Cucin | |
| 2006/0135974 A1* | 6/2006 | Perkins | A61M 1/0058 606/169 |
| 2006/0173426 A1 | 8/2006 | Urich et al. | |
| 2006/0253062 A1* | 11/2006 | Liao | A61F 9/00745 604/27 |
| 2006/0259117 A1* | 11/2006 | Pal | 623/1.11 |
| 2006/0271082 A1 | 11/2006 | Kirchhevel et al. | |
| 2007/0088376 A1 | 4/2007 | Zacharias | |
| 2007/0100362 A1 | 5/2007 | Deng | |
| 2007/0173870 A2 | 7/2007 | Zacharias | |
| 2007/0185512 A1 | 8/2007 | Kirchhevel | |
| 2007/0185514 A1 | 8/2007 | Kirchhevel | |
| 2007/0250039 A1* | 10/2007 | Lobbins | A61M 25/0012 604/523 |
| 2008/0004568 A1* | 1/2008 | Jeffrey | A61M 25/0069 604/96.01 |
| 2008/0110236 A1 | 5/2008 | Hajishah et al. | |
| 2008/0146988 A1 | 6/2008 | Olivera et al. | |
| 2008/0149197 A1 | 6/2008 | Turner et al. | |
| 2008/0172077 A1 | 7/2008 | Valencia et al. | |
| 2008/0262476 A1 | 10/2008 | Krause et al. | |
| 2009/0030372 A1* | 1/2009 | Finodeyev | A61M 1/0001 604/122 |
| 2009/0088784 A1 | 4/2009 | DeBoer et al. | |
| 2009/0203480 A1 | 8/2009 | Petzold et al. | |
| 2009/0259242 A1 | 10/2009 | Gerg et al. | |
| 2009/0281479 A1 | 11/2009 | Gagnepain et al. | |
| 2010/0056991 A1 | 3/2010 | Dimalanta, Jr. et al. | |
| 2010/0063437 A1 | 3/2010 | Nelson et al. | |
| 2010/0100112 A1 | 4/2010 | Kauker et al. | |
| 2010/0145374 A1 | 6/2010 | Perkins et al. | |
| 2010/0152614 A1 | 6/2010 | Mark | |
| 2010/0152762 A1 | 6/2010 | Mark | |
| 2010/0191177 A1* | 7/2010 | Chang et al. | 604/22 |
| 2010/0305596 A1 | 12/2010 | Peterson et al. | |
| 2011/0005387 A1 | 1/2011 | Ehre et al. | |
| 2011/0144675 A1 | 6/2011 | Gao et al. | |
| 2011/0184374 A1* | 7/2011 | Gao | A61M 5/14232 604/500 |
| 2011/0204622 A1 | 8/2011 | Lewis et al. | |
| 2011/0245775 A1* | 10/2011 | Tekulve | A61M 25/0045 604/171 |
| 2011/0295292 A1 | 12/2011 | Hsia | |
| 2011/0299943 A1 | 12/2011 | Woolever | |
| 2012/0055329 A1 | 3/2012 | Heer | |
| 2012/0157912 A1* | 6/2012 | Sorensen | A61F 9/00745 604/28 |
| 2013/0047739 A1 | 2/2013 | Schmidt et al. | |
| 2013/0325044 A1* | 12/2013 | Wang et al. | 606/161 |
| 2014/0171995 A1* | 6/2014 | McDonell | A61F 9/00736 606/170 |
| 2014/0171996 A1* | 6/2014 | McDonell | A61F 9/00763 606/171 |
| 2016/0128870 A1* | 5/2016 | Mcdonell | A61B 17/00 606/171 |
| 2016/0135991 A1* | 5/2016 | Farley | A61F 9/00763 606/171 |

FOREIGN PATENT DOCUMENTS

| | | |
|---|---|---|
| DE | 102 47 869 A1 | 5/2004 |
| DE | 102006030034 A | 1/2008 |
| EP | 0 626 628 A1 | 11/1994 |
| EP | 0 469 641 B1 | 12/1995 |
| EP | 630494 B1 | 7/1996 |
| EP | 495044 B1 | 9/1998 |
| EP | 0874163 A2 | 10/1998 |
| EP | 0874163 A3 | 3/1999 |
| EP | 1074271 A2 | 2/2001 |
| EP | 1199053 | 4/2002 |
| EP | 1390979 | 2/2004 |
| EP | 1074271 B1 | 10/2004 |
| EP | 1123049 B1 | 1/2007 |
| FR | 2 816 823 A1 | 5/2002 |
| FR | 2905594 A1 | 3/2008 |
| FR | 3006214 B1 | 11/2015 |
| GB | 792397 | 3/1958 |
| GB | 1189493 A | 4/1970 |
| GB | 1213723 A | 11/1970 |
| GB | 1323788 | 7/1973 |
| GB | 1390979 | 4/1975 |
| GB | 1417299 | 12/1975 |
| GB | 2140871 | 12/1984 |
| GB | 2203195 A | 10/1988 |
| JP | 07259801 A | 10/1995 |
| JP | 08243080 A | 9/1996 |
| JP | H0-9225698A A | 9/1997 |
| JP | 2002-125995 | 5/2002 |
| JP | 2002125995 | 5/2002 |
| JP | 2008543385 | 12/2008 |
| JP | 2010-057642 A | 3/2010 |
| UA | 78244 C2 | 3/2007 |
| WO | 93/02627 A1 | 2/1993 |
| WO | 93/05718 A1 | 4/1993 |
| WO | 98/25556 A1 | 6/1998 |
| WO | 00/22994 A1 | 4/2000 |
| WO | 00/78371 A1 | 12/2000 |
| WO | 01/30281 A1 | 5/2001 |
| WO | 2005/028126 A1 | 3/2005 |
| WO | 2008/029066 A1 | 3/2008 |
| WO | 2010/066302 A1 | 6/2010 |
| WO | 2013/085758 A1 | 6/2013 |

OTHER PUBLICATIONS

International Searching Authority, International Search Report, PCT/US2012/066714, dated Apr. 19, 2013, 4 pages.

International Searching Authority, Written Opinion of the International Searching Authority, PCT/US2012/066714, dated Apr. 19, 2013, 5 pages.

Kabei, Shimemura, et al., A portable pneumatic driving unit for a left ventricular assist device, Int. J. Artif. Organs, 1988, 186-90, 11(3).

Nachlas, Marvin, et al., A simple portable pneumatic pump for external cardiac massage, The American Journal of Cardiology, 1962, 107-109, 10(1).

Waldeck, J.L., The development of a portable pressure source for the static and dynamic calibration of pressure transducers, The Journal of Wind Engineering and Industrial Aerodynamics, 1987, 213-230, 26(2).

Ellis, George, et al., Microcomputer-Controlled Precision Pressure Generator, IEEE Transactions on Instrumentation and Measurement, 1977, 214-217, 26(3).

Whalen, R.L., et al., An electromagnetic pneumatic blood pump driver, American Society of Artificial Internal Organs, 1988, 721-725, 34(3).

(56) References Cited

OTHER PUBLICATIONS

Turkentine, R.B., et al., Pressure-operated shutter for thin-film monitor, Journal of Physics E: Scientific Instruments, 1979, 12(1).
Rogers, Richard C., An inexpensive picoliter-volume pressure ejection system, Brain Research Bulletin, 1985, 669-671, 15(6).
Johnson, Kenneth S., et al., A submersible flow analysis System, Analytical Chimica Acta, 1986, 245-257, 179.
Tabassum, Alim Abid, Solar refrigeration: evaluation of technical options and design of a solar-generator-adsorber for a novel adsorption refrigerator, Tabassum thesis, Cranfield University, 1989.
Buchanan, P.R., et al., Recovery of ventilation distributions by gas wash-out of a mechanical pump, Clinical Physics and Physiological Measurement, 1986, 7(3).
Supplementary European Search Report and Annex to the European Search Report issued for EP Application No. 12856463 dated Jul. 17, 2014, 6 pgs.
English translation of Japanese Office Action issued for JP 2014-544825 dated Jun. 25, 2015, 4 pgs.
Jack D. Hilbert, "How to Get a Pneumatic Conveying Pipeline to Handle More" http://www.powderandbulk.com/pb_services/ask_joe_archive/how_to_get_a_pneumatic_conveying_pipeline_to_handle_more.htm, visited Mar. 1, 2010, 5 pages.
English Translation of Chinese Office Action issued for CN 201280060091.7 dated Nov. 3, 2015, 12 pgs.
JP Office Action, Application No. 2014-544825, dated Jan. 29, 2016, 4 pgs., no translation.

\* cited by examiner

OPTIMIZED PNEUMATIC DRIVE LINES

BACKGROUND OF THE INVENTION

The present disclosure relates generally to a pneumatic drive line having a non-uniform internal cross-section that is used to drive pneumatic surgical instruments in surgical procedures such as, for example, a vitrectomy procedure.

A vitrectomy procedure may be performed to clear blood and debris from the eye, to remove scar tissue, or to alleviate traction on the retina. Blood, inflammatory cells, debris, and scar tissue may obscure light as it passes through the eye to the retina, resulting in blurred vision. The vitreous may also be removed if it is pulling or tugging the retina from its normal position. Some of the most common eye conditions that require vitrectomy include complications from diabetic retinopathy such as retinal detachment or bleeding, macular hole, retinal detachment, pre-retinal membrane fibrosis, bleeding inside the eye (vitreous hemorrhage), injury or infection, and certain problems related to previous eye surgery.

In a vitrectomy, the surgeon may create three tiny incisions in the eye for three separate instruments. These incisions may be placed in the pars plana of the eye, which is located just behind the iris but in front of the retina. The instruments which pass through these incisions may include a light pipe, an infusion port, and the vitrectomy cutting device. The light pipe is the equivalent of a microscopic high-intensity flashlight for use within the eye. The infusion port may be used to replace fluid in the eye and maintain proper pressure within the eye. The vitrectomy probe, or cutting device, may work like a tiny guillotine, with an oscillating microscopic cutter to remove the vitreous gel in a controlled fashion. This may prevent significant traction on the retina during the removal of the vitreous humor.

Traditionally, the vitrectomy probe is connected to a surgical machine that is used to perform the vitrectomy procedure and other surgeries on the posterior of the eye. The surgical machine may provide power to and control the operation of the attached vitrectomy probe. In order to provide pneumatic power to the vitrectomy probe, the surgical machine may include a pneumatic or air distribution module. This pneumatic module may condition and supply compressed air or gas to power the probe. The pneumatic module may be connected to a cylinder that contains compressed gas.

Typically, the surgical machine connects to a vitrectomy probe via a tubing. Such tubing traditionally has a constant inside diameter along the length of the tubing. Thus, the size of the passageway within the tubing remains the same as the pressurized gas travels from the surgical machine to the vitrectomy probe. This results in a tube having the same degree of flexibility throughout the length of the tube. Additionally, because the tubing has a constant inside diameter along the length of the tubing, the tubing is not optimized for pneumatic performance.

SUMMARY OF THE INVENTION

In one exemplary aspect, the present disclosure is directed to a system. The system includes a pneumatic surgical instrument and a surgical console operable to provide compressed gas to the pneumatic surgical instrument. Additionally, the system includes a pneumatic drive line coupling the pneumatic surgical instrument to the surgical console. The pneumatic drive line has an internal bore configured to deliver the compressed gas to the pneumatic surgical instrument. The internal bore has a non-uniform cross-section along a length of the pneumatic drive line.

In one exemplary aspect, the present disclosure is directed to a system. The system includes a pneumatic surgical instrument and a source of compressed gas. Also, the system has a pneumatic drive line coupling the pneumatic surgical instrument to the source. The pneumatic drive line has a passageway extending therethrough that is sized and shaped to deliver the compressed gas to the pneumatic surgical instrument. The passageway has a non-uniform diameter from the source of the compressed gas to the pneumatic surgical instrument.

In one exemplary aspect, the present disclosure is directed to a system. The system includes a pneumatic drive line operable to drive a pneumatic surgical instrument. The pneumatic drive line including a passageway extending therethrough to provide compressed gas to the pneumatic surgical instrument. The passageway has a non-uniform cross-section along a length of the pneumatic drive line.

These and other aspects, forms, objects, features, and benefits of the present disclosure will become apparent from the following detailed drawings and description.

BRIEF DESCRIPTION OF THE DRAWINGS

The accompanying drawings, which are incorporated in and constitute a part of the specification, illustrate embodiments of the present disclosure. Together with a general description of the present disclosure given above, and the detailed description given below, the drawings serve to exemplify the embodiments of the present disclosure.

DETAILED DESCRIPTION OF THE INVENTION

Figure 1:
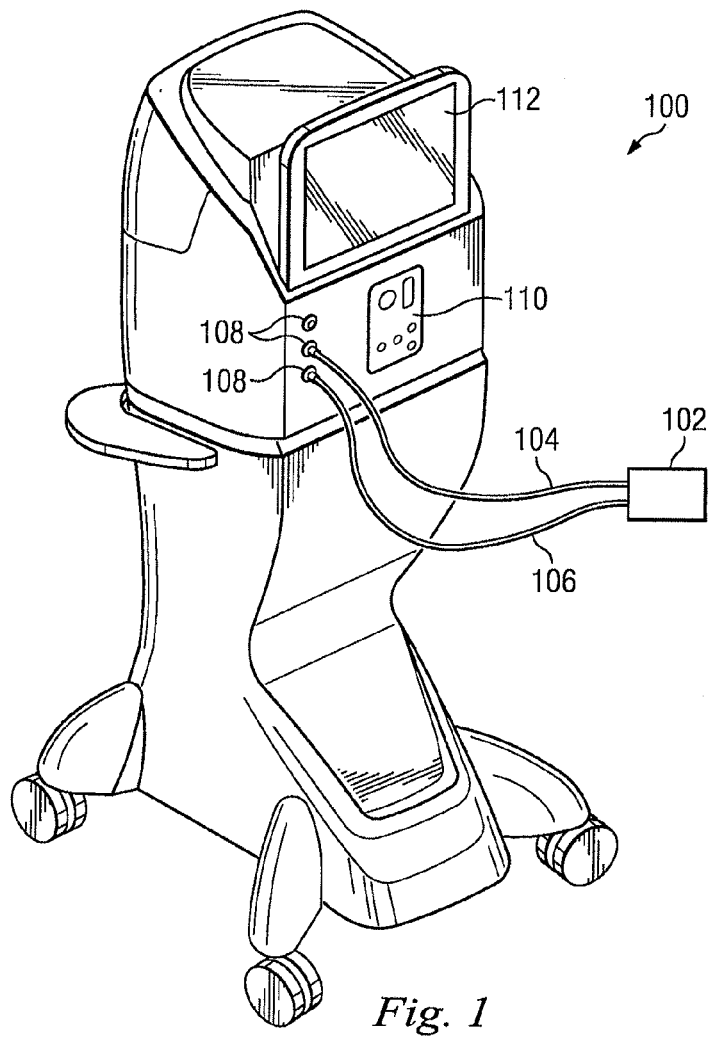
FIG. 1 is an illustration of an exemplary surgical console for performing various ophthalmic procedures including a vitrectomy according to one aspect of the present disclosure.

The present disclosure relates generally to the field of ophthalmic surgery, and more particularly to a pneumatic drive line having a non-uniform internal cross-section and/or diameter that is used to drive pneumatic surgical instruments in surgical procedures such as, for example, a vitrectomy procedure. For the purposes of promoting an understanding of the principles of the present disclosure, reference will now be made to embodiments or examples illustrated in the drawings, and specific language will be used to describe these examples. It will nevertheless be understood that no limitation of the scope of the present disclosure is thereby intended. Any alteration and further modifications in the described embodiments, and any further applications of the principles of the present disclosure as described herein are contemplated as would normally occur to one skilled in the art to which the disclosure relates.

FIG. 1 is an illustration of an exemplary surgical console 100 for performing various ophthalmic surgical procedures. In that regard, surgical console 100 is configured to assist a user in performing a vitrectomy procedure. More specifically, surgical console 100 is configured to drive pneumatic surgical instrument 102. Here, pneumatic surgical instrument 102 is a vitrectomy probe. However, in other embodiments, pneumatic surgical instrument 102 can be any other pneumatic surgical instruments powered by a pneumatic drive line.

As shown in FIG. 1, pneumatic surgical instrument 102 is coupled to surgical console 100 via pneumatic drive lines 104 and 106, or tubing. Here, surgical console 100 has ports 108 designed to couple pneumatic drive lines 104 and 106 to the surgical console 100. As discussed in greater detail below, pneumatic drive lines 104 and 106 provide power to pneumatic surgical instrument 102. That is, surgical console 100 provides a compressed gas, such as nitrogen, through pneumatic drive lines 104 and 106 to drive and/or power pneumatic surgical instrument 102. Although FIG. 1 shows two separate pneumatic drive lines powering pneumatic surgical instrument 102, other embodiments utilize a single pneumatic drive line or more than two pneumatic drive lines. Thus, no limitation to the number of pneumatic drive lines is implied herein to power pneumatic surgical instrument 102.

Additionally, surgical console 100 also includes a fluidics module 110. Fluidics module 110 is configured to support irrigation and/or aspiration functions during a surgical procedure. In other words, although not shown, pneumatic surgical instrument 102 can be coupled to fluidics module 110 via additional tubings configured to support irrigation and/or aspiration functions with respect to pneumatic surgical instrument 102 or any other instrument connected to surgical console 100.

Additionally, surgical console 100 includes a display 112. Display 112 is operable to display information to a user of the console. In that regard, display 112 provides visual information relevant to the operation of pneumatic surgical instrument 102. Also, display 112 may be a touchscreen display that receives user input and assist in ease of operation for a user of console 100.

Figure 2:
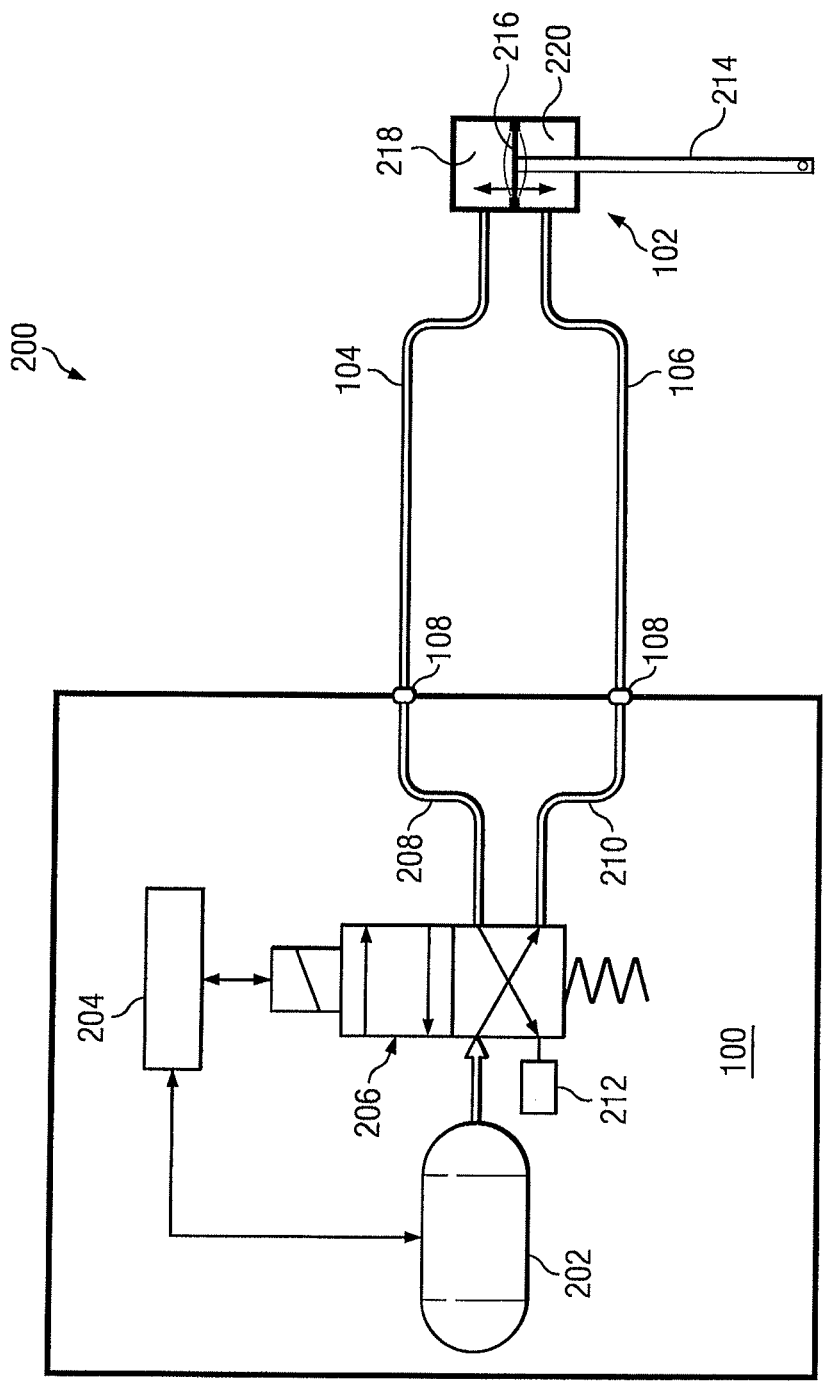
FIG. 2 is a schematic diagram of a pneumatic system for powering a surgical instrument according to one aspect of the present disclosure.

Referring to FIG. 2, a schematic diagram of a pneumatic system 200 for powering pneumatic surgical instrument 102 is shown. As shown, surgical console 100 includes a source 202 of compressed gas, such as nitrogen, that is used to power and/or drive pneumatic surgical instrument 102. Pneumatic system 200 also includes a controller 204. Controller 204 is in communication with source 202 and is configured to regulate the pressure of the compressed gas within source 202. In that regard, controller 204 regulates pressure within source 202 by balancing between lower pressures that allow for reduction in gas consumption and higher pressures that allow for faster driving of pneumatic surgical instrument 102 (e.g. allow for faster cut rates and/or increase a dynamic range of available cut rates for pneumatic surgical instrument 102). In other embodiments, the pressure within source 202 may also be regulated by a separate controller that is external to the surgical console 100.

As shown in FIG. 2, the pneumatic system 200 includes pneumatic valve 206. Pneumatic valve 206 is coupled to source 202 and channels 208 and 210. Also, pneumatic valve 206 is in communication with controller 204. Here, pneumatic valve 206 is a four-way valve. However, other valve configurations are also contemplated for pneumatic valve 206.

Pneumatic valve 206 includes a solenoid that operates to move the valve 206 to one of two positions as directed by control signals from controller 204. In a first position, pneumatic valve 206 allows pressurized gas from source 202 to pass through pneumatic valve 206 to channel 210 to provide pneumatic power to pneumatic surgical instrument 102 via pneumatic drive line 106 while venting pressurized gas from pneumatic drive line 104 via channel 208 through muffler 212. In a second position, pneumatic valve 206 allows pressurized gas from source 202 to pass through pneumatic valve 206 to channel 208 to provide pneumatic power to pneumatic surgical instrument 102 via pneumatic drive line 104 while venting pressurized gas from pneumatic drive line 106 via channel 210 through muffler 212.

As discussed above, pneumatic surgical instrument 102 is a vitrectomy probe. As shown in FIG. 2, pneumatic surgical instrument 102 has a probe cutter 214 and dual chambers separated by a diaphragm 216. In that regard, pneumatic drive line 104 is coupled to an in communication with first chamber 218 and pneumatic drive line 106 is coupled to an in communication with second chamber 220.

Accordingly, when the pneumatic valve 206 is in the first position, the second chamber 220 of pneumatic surgical instrument 102 is charged by being filled with pressurized gas delivered via pneumatic drive line 106 while the first chamber 218 is discharged by the release of pressurized gas into pneumatic drive line 104. Moreover, when the pneumatic valve 206 is in the second position, the first chamber 218 of pneumatic surgical instrument 102 is charged by being filled with pressurized gas delivered via pneumatic drive line 104 while the second chamber 220 is discharged by the release of pressurized gas into pneumatic drive line 106. As will be described in greater detail below, the switching of the pneumatic valve 206 between the first and second positions causes the diaphragm 216 to oscillate or move the probe cutter 214 in order to cut vitreous tissue within a patient's eye.

Figure 3:
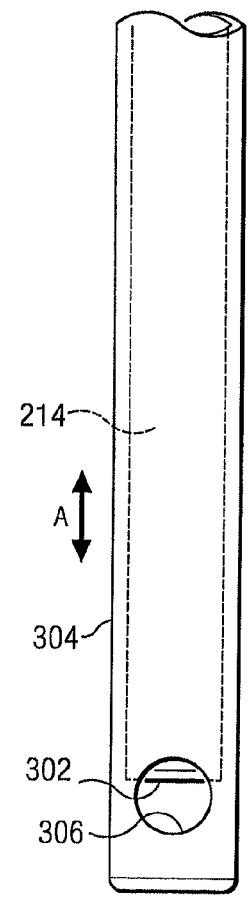
FIG. 3 is an illustration of a probe cutter of the surgical instrument of FIG. 2 according to one aspect of the present disclosure.

Referring to FIG. 3 an illustration of probe cutter 214 of the pneumatic surgical instrument 102 is shown. As discussed above, the switching of the pneumatic valve 206 between the first and second positions causes the diaphragm 216 to oscillate or move the probe cutter 214. This movement or oscillation by probe cutter 214 is identified by arrow A.

Probe cutter 214 acts as a cutting device. In that regard, probe cutter 214 has a sharpened end 302 and is surrounded in part by an outer tube 304. Also, outer tube 304 includes a cutter port 306, or opening. Because the probe cutter 214 moves back and forth within outer tube 304 as identified by arrow A, the probe cutter 214 alternately opens and closes cutter port 304 with sharpened end 302 of the probe cutter 214. As such, the opening and closing of cutter port 304 with sharpened end 302 of the probe cutter 214 can cut through material placed adjacent the probe cutter, such as vitreous in a patient's eye during a vitrectomy.

Figure 4:
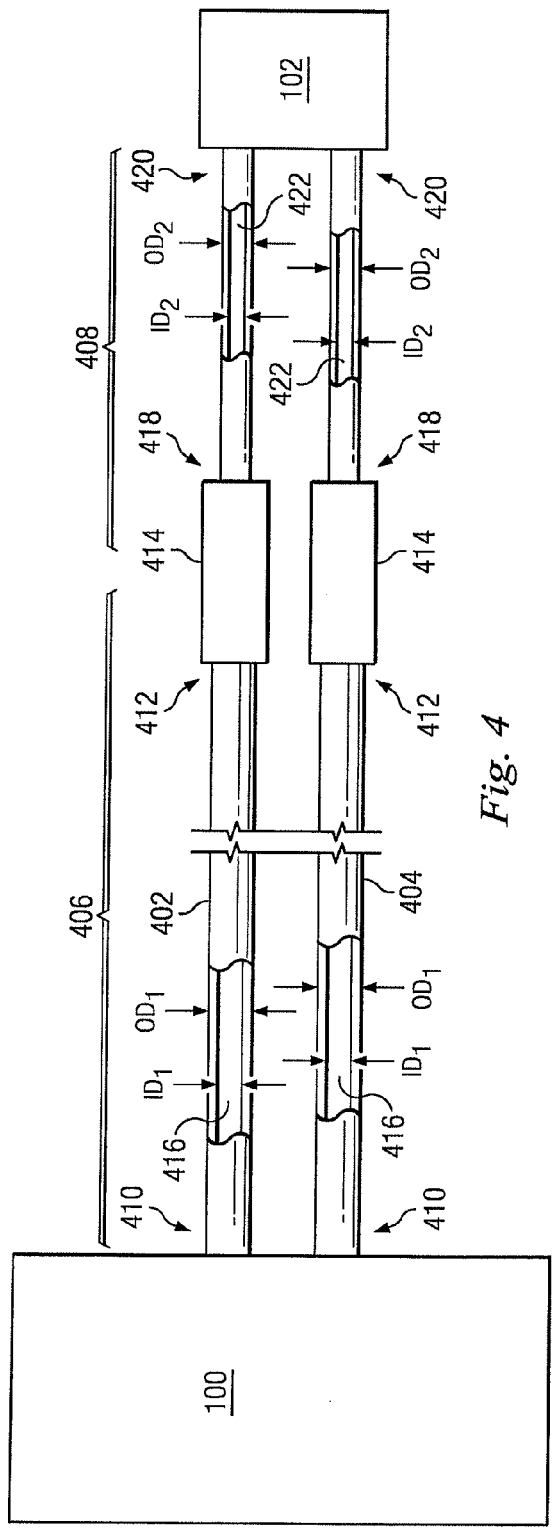
FIG. 4 is an illustration of a partial cross-sectional view of stepped pneumatic drive lines usable with the pneumatic system shown in FIG. 2 according to one aspect of the present disclosure.

FIG. 4 is an illustration of a partial cross-sectional view of stepped pneumatic drive lines usable with pneumatic system 200 to drive pneumatic surgical instrument 102. As shown, surgical console 100 and pneumatic surgical instrument 102 are coupled to stepped pneumatic drive lines 402 and 404. Stepped pneumatic drive lines 402 and 404 are used in system 200 in place of pneumatic drive lines 104 and 106, respectively. As such, all description herein related to pneumatic drive lines 104 and 106 is applicable to stepped pneumatic drive lines 402 and 404 unless stated otherwise.

Stepped pneumatic drive line 402 will be described below. The features discussed with respect to stepped pneumatic drive line 402 are present in and equally applicable to stepped pneumatic drive line 404. As such, similar reference numerals have been used in FIG. 4 to identify similar features with respect to stepped pneumatic drive lines 402 and 404.

Also, even though FIG. 4 shows two separate stepped pneumatic drive lines 402 and 404 powering pneumatic surgical instrument 102, other embodiments utilize a single stepped pneumatic drive line or more than two stepped pneumatic drive lines. Thus, no limitation to the number of stepped pneumatic drive lines is implied herein to power pneumatic surgical instrument 102.

Stepped pneumatic drive line 402 has a first segment 406 and a second segment 408. The first segment 406 has a proximal end 410 that is coupled to surgical console 100 via ports 108 and a distal end 412 that is coupled to the second segment 406 via a sleeve 414, or coupler. Additionally, the first segment includes an internal bore 416, or passageway extending from the proximal end 410 to the distal end 412 of the first segment 406.

Although sleeve 414 is shown coupling the first segment 406 and the second segment 408, it is contemplated that any other means can be used to couple the two segments together. For example, in other embodiments one of the segments is configured to be slid into the other segment thereby coupling the segments without the use of sleeve 414. Additionally, in other embodiments, the pneumatic drive line 402 is manufactured as a continuous drive line having the two or more segments with the stepped configuration. In such an embodiment, the pneumatic drive line does not require the sleeve coupling the segments because the segments have been manufactured into a continuous drive line having the stepped configuration.

As shown, first segment 406 has a substantially constant outside diameter $OD_1$ from the proximal end 410 to the distal end 412 of the first segment 406. By way of example, and not by limitation, $OD_1$ can be about 0.250 inches. Moreover, $OD_1$ can range from about 0.15 inches to about 0.5 inches. However, other dimensions for $OD_1$ are contemplated thereby no implied limitation is set forth herein.

Additionally, internal bore 416 of first segment 406 has a substantially constant inside diameter $ID_1$ extending from the proximal end 410 to the distal end 412 of the first segment 406. By way of example, and not by limitation, $ID_1$ can be about 0.150 inches. Moreover, $ID_1$ can range from about 0.1 inches to about 0.3 inches. However, other dimensions for $ID_1$ are contemplated thereby no implied limitation is set forth herein.

Second segment 408 has a proximal end 418 that is coupled to the first segment 406 via sleeve 414 and a distal end 420 that is coupled to pneumatic surgical instrument 102. Additionally, the second segment 408 includes an internal bore 422, or passageway extending from the proximal end 418 to the distal end 420 of the second segment 408.

As shown, second segment 408 has a substantially constant outside diameter $OD_2$ from the proximal end 418 to the distal end 420 of the second segment 408. By way of example, and not by limitation, $OD_2$ can be about 0.125 inches. Furthermore, $OD_2$ can range from about 0.05 inches to about 0.20 inches. However, other dimensions for $OD_2$ are contemplated thereby no implied limitation is set forth herein.

Additionally, internal bore 422 of second segment 408 has a substantially constant inside diameter $ID_2$ extending from the proximal end 418 to the distal end 420 of the second segment 408. By way of example, and not by limitation, $ID_2$ can be about 0.06 inches. Furthermore, $ID_2$ can range from about 0.01 inches to about 0.150 inches. However, other dimensions for $ID_2$ are contemplated thereby no implied limitation is set forth herein.

Accordingly, the second segment 408 is "stepped" down relative to the first segment 406. In that regard, the outside diameter $OD_1$ of the first segment 406 is greater than the outside diameter $OD_2$ of the second segment 408. Moreover, the inside diameter $ID_1$ of the first segment 406 is greater than the inside diameter $ID_2$ of the second segment 408. Therefore, because the second segment 408 is "stepped" down from the first segment 406, the passageway extending through stepped pneumatic drive line 402 has a non-uniform cross-section and/or diameter as the pneumatic drive line extends from surgical console 100 to pneumatic surgical instrument 102.

Based on this stepped configuration, stepped pneumatic drive line 402 increases the performance of pneumatic surgical instrument 102 in comparison to other pneumatic instruments using traditional pneumatic drive line tubing. As discussed above, traditional pneumatic drive line tubing has a constant inside diameter along the length of the tubing. Thus, the size of the passageway within the tubing remains the same as the pressurized gas travels from the surgical console to the surgical instrument.

By contrast, stepped pneumatic drive line 402 has a non-constant or non-uniform inside diameter (or cross-section) along the length of the drive line. The use of a non-constant inside diameter allows stepped pneumatic drive line 402 to be optimized based on its functional needs along its length. Because stepped pneumatic drive line 402 can be considered closed at its end coupled to pneumatic surgical instrument 102 and is being driven from the end of the line coupled to console 100, the driven end of stepped pneumatic drive line 402 has a higher gas flow requirement. Thus, in order to optimize gas flow, the driven end of stepped pneumatic drive line 402 should have a larger diameter than the closed end.

Here, first segment 406 has a larger inside diameter $ID_1$ for internal bore 416 than the inside diameter $ID_2$ for internal bore 422 of segment 408. As such, internal bore 416 allows for a larger volume of pressurized gas to be received into the line from console 100 where high flow of pressured gas is most important in order to optimize pneumatic performance.

Additionally, as discussed above, the use of a non-constant inside diameter allows stepped pneumatic drive line 402 to be optimized based on its functional needs along its length. In that regard, because traditional pneumatic drive lines have constant diameters, the portion of the drive line adjacent the surgical instrument still has the same large inside diameter required at the other end being driven by the surgical console. As such, the tubing has a larger than ideal size and mass and as a result the tubing is typically not as flexible as would be desirable near the surgical instrument.

Stepped pneumatic drive line 402 addresses this issue. As discussed above, stepped pneumatic drive line 402 includes second segment 408 having a smaller inside diameter $ID_2$ and outside diameter $OD_2$ than the inside diameter $ID_1$ and outside diameter $OD_1$ of segment 406. As such, stepped pneumatic drive line 402 provides a smaller drive line (e.g. second segment 408) adjacent the pneumatic surgical instrument 102 where high flexibility and low mass are most important for a user of pneumatic surgical instrument 102. Therefore, stepped pneumatic drive line 402 tubing is configured to provide greater flexibility and a low mass while still optimizing pneumatic performance.

Figure 5:
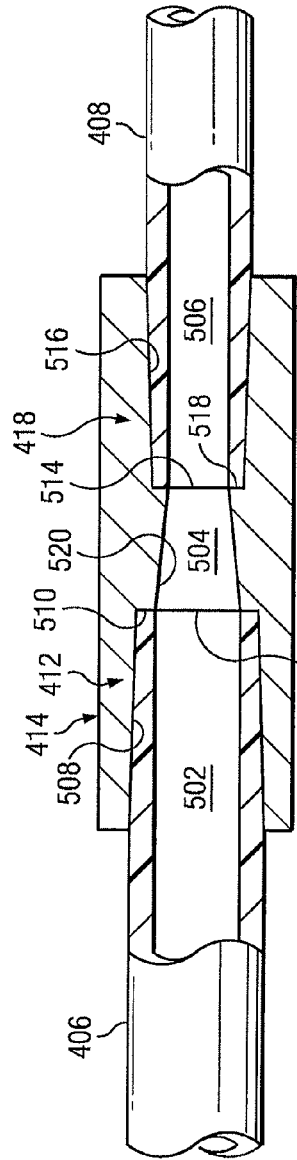
FIG. 5 is an illustration of a partial cross-sectional view of a sleeve coupling the stepped pneumatic drive line shown in FIG. 4 according to one aspect of the present disclosure.

FIG. 5 shows a partial cross-sectional view of sleeve 414 coupling the distal end 412 of the first segment 406 to the proximal end 418 of the second segment 408. As shown, sleeve 414 has a proximal bore 502, connecting bore 504, or middle bore, and a distal bore 506. Proximal bore 502 is sized and shaped for receiving distal end 412 of the first segment 406.

Moreover, proximal bore 502 is defined in part by interior surface 508 of sleeve 414. In that regard, interior surface 508 is tapered or sloped towards connecting bore 504. As a result, distal end 412 of the first segment 406 is coupled to sleeve 414 via a press-fit or sealing engagement by the tapered interior surface 508 applying a coupling force against the distal end 412.

Additionally, proximal bore 502 includes stops 510. Stops 510 prevents the distal end 412 from extending into connecting bore 504. In that regard, distal end 412 of the first segment 406 abuts against the stops 510 when fully inserted into sleeve 414. Thus, stops 510 prevent over insertion of distal end 412 into sleeve 414.

Distal bore 506 is sized and shaped for receiving proximal end 418 of the second segment 408. Distal bore 506 is defined in part by interior surface 516 of sleeve 414. In that regard, interior surface 516 is tapered or sloped towards connection bore 504. As a result, proximal end 418 of the second segment 408 is coupled to sleeve via a press-fit or sealing engagement by the tapered interior surface applying a coupling force against the proximal end 418.

Additionally, distal bore 506 includes stops 518. Stops 518 prevents the proximal end 418 from extending into connecting bore 504. In that regard, proximal end 418 of the second segment 408 abuts against the stops 518 when fully inserted into sleeve 414. Thus, stops 518 prevent over insertion of proximal end 418 into sleeve 414.

As shown, connecting bore 504 is positioned between the proximal bore 502 and the distal bore 506. Connecting bore has a conical shape. In that regard, interior surface 520 defines connecting bore 504 and tapers toward distal bore 506. As such, opening 512 of connecting bore 504 adjacent the proximal bore 502 has a larger diameter than opening 514 adjacent the distal bore 506. Moreover, opening 512 has a diameter substantially similar to the inside diameter $ID_1$ of internal bore 416 of the first segment 406. Additionally, opening 514 has a diameter substantially similar to the inside diameter $ID_2$ of internal bore 422 of the second segment 408. Because of the sizing of openings 512 and 514 and the conical shape of connecting bore 504, a seal is formed between internal bore 416 of the first segment and internal bore 422 of the second segment 408 that enables pressurized gas to flow therethrough.

Figure 6:
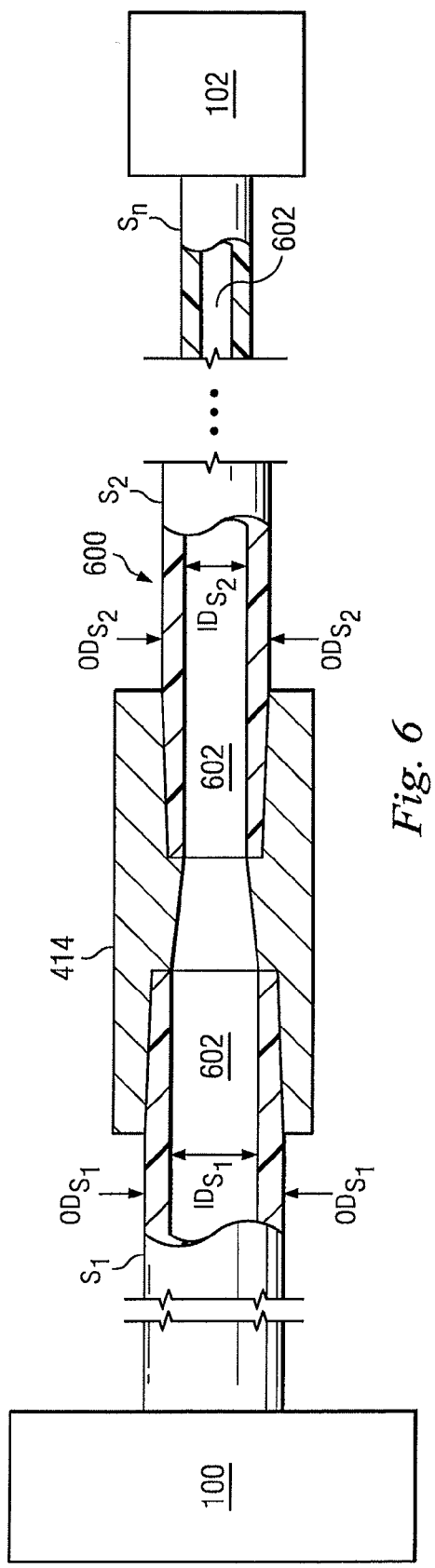
FIG. 6 is an illustration of a partial cross-sectional view of an alternative embodiment of a stepped pneumatic drive line usable with pneumatic system shown in FIG. 2 according to one aspect of the present disclosure.

FIG. 6 is an illustration of a partial cross-sectional view of an alternative embodiment of a stepped pneumatic drive line 600 usable with pneumatic system 200. As shown, surgical console 100 and pneumatic surgical instrument 102 are coupled to stepped pneumatic drive line 600. Stepped pneumatic drive line 600 is used in system 200 in place of pneumatic drive line 104 or 106. As such, all description herein related to pneumatic drive lines 104 and 106 is applicable to stepped pneumatic drive line 600 unless stated otherwise.

Also, even though FIG. 6 shows a single stepped pneumatic drive line powering pneumatic surgical instrument 102, other embodiments utilize more than one stepped pneumatic drive line 600. Thus, no limitation to the number of stepped pneumatic drive lines 600 is implied herein to power pneumatic surgical instrument 102.

Stepped pneumatic drive line 600 is substantially similar to stepped pneumatic drive line 402. However, stepped pneumatic drive line 600 has more than two segments where each adjacent segment are each coupled by a sleeve 414. Here, the segments are identified by segment $S_1$ through $S_n$ where n represents the cumulative number of segments coupled together. Thus, stepped pneumatic drive line 600 can be comprised of any number of segments.

In that regard, segment $S_1$ adjacent surgical console 100 has an internal bore having the largest internal diameter $ID_{S1}$ relative to any other segment in stepped pneumatic drive line 600. In other words, as one moves from segments $S_1$ to the next segment the inside diameter (e.g. $ID_{S2}$) of the bore of the adjacent segment (e.g. $S_2$) is smaller than the inside diameter ($ID_{S1}$) of the previous segment (e.g. $S_1$) and so forth. Thus, internal passageway 602 extending through pneumatic drive line 600 decreases in diameter from the end adjacent console 100 to the end adjacent pneumatic surgical instrument 102 resulting in a "stepped", "bumped", and/or "bumped tubing" drive line.

Accordingly, because pneumatic drive line 600 has a non-constant inside diameter along passageway 602, the stepped pneumatic drive line is optimized based on its functional needs along its length. In that regard, pneumatic drive line 600 allows for a larger volume of pressurized gas to be received into the line from console 100 as compared to the size of the inside diameter of drive line adjacent pneumatic surgical instrument 102. Thus, pneumatic drive line 600 allows for a larger volume of pressurized gas to be received into the line from console 100 where high flow of pressured gas is most important in order to optimize pneumatic performance.

Moreover, stepped pneumatic drive line 600 provides a smaller drive line (e.g. segment $S_n$) adjacent the pneumatic surgical instrument 102 where high flexibility and low mass are most important for a user of pneumatic surgical instrument 102. As shown in FIG. 6, as one moves from segment $S_1$ to the next segment the inside diameter (e.g. $ID_{S2}$) of the bore of the adjacent segment (e.g. $S_2$) is smaller than the inside diameter (e.g. $ID_{S1}$) of the previous segment (e.g. $S_1$) and so forth. Additionally, as one moves from segment $S_1$ to the next segment the outside diameter (e.g. $OD_{S2}$) of the adjacent segment (e.g. $S_2$) is smaller than the outside diameter (e.g. $OD_1$) of the previous segment (e.g. $S_1$) and so forth. Thus, stepped pneumatic drive line 600 provides a smaller drive line (e.g. $S_n$) adjacent the pneumatic surgical instrument 102 where high flexibility and low mass are most important for a user of pneumatic surgical instrument 102. Accordingly, stepped pneumatic drive line 600 is configured to provide greater flexibility and a low mass while still optimizing pneumatic performance as compared to a traditional pneumatic drive line.

Figure 7:
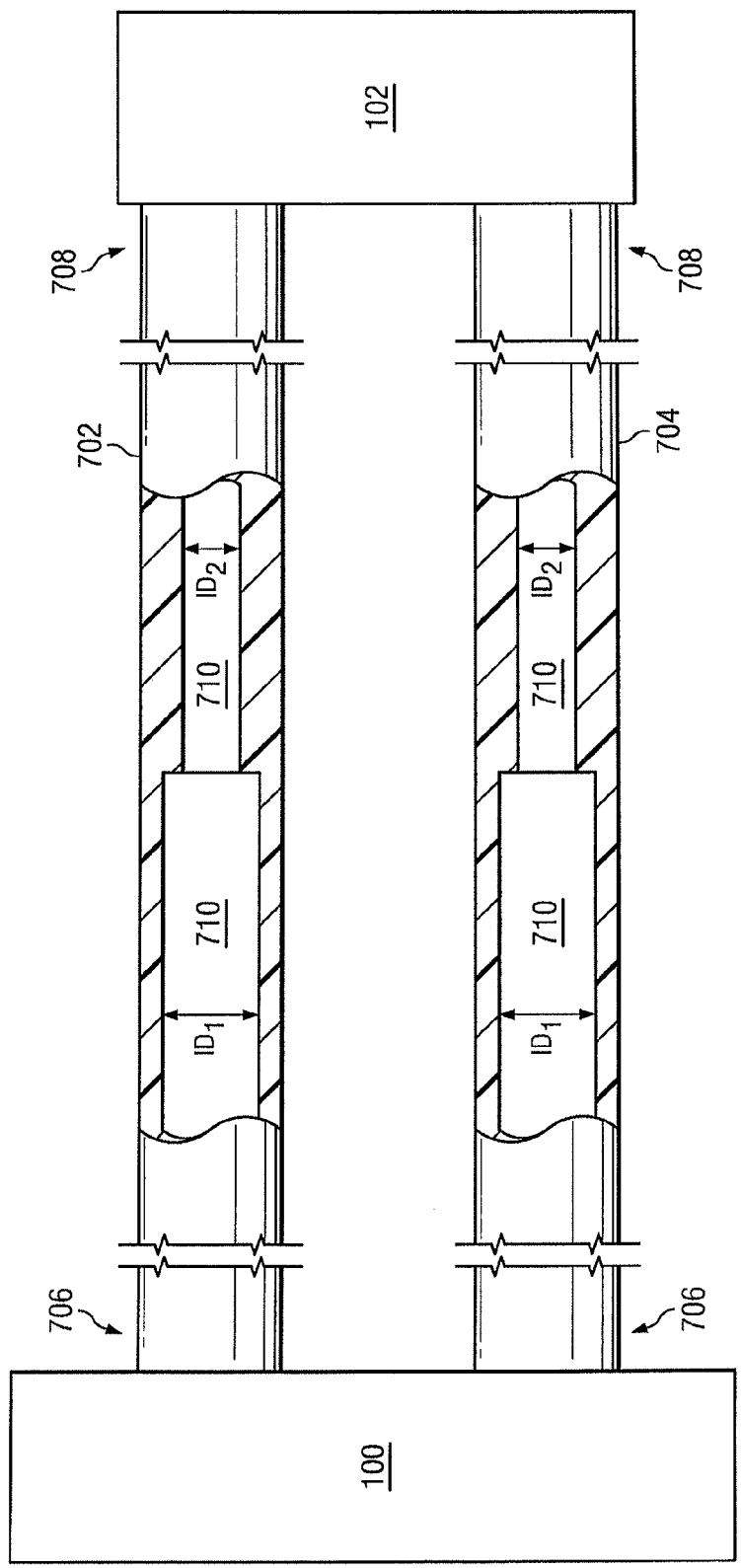
FIG. 7 is an illustration of a partial cross-sectional view of an alternative embodiment of stepped pneumatic drive lines usable with the pneumatic system shown in FIG. 2 according to one aspect of the present disclosure.

FIG. 7 is an illustration of a partial cross-sectional view of an alternative embodiment of stepped pneumatic drive lines usable with the pneumatic system 200. As shown, surgical console 100 and pneumatic surgical instrument 102 are coupled to stepped pneumatic drive lines 702 and 704. Stepped pneumatic drive lines 702 and 704 are used in system 200 in place of pneumatic drive lines 104 and 106, respectively. As such, all description herein related to pneumatic drive lines 104 and 106 is applicable to stepped pneumatic drive lines 702 and 704 unless stated otherwise.

Stepped pneumatic drive line 702 will be described below. The features discussed with respect to stepped pneumatic drive line 702 are present in and equally applicable to stepped pneumatic drive line 704. As such, similar reference numerals have been used in FIG. 7 to identify similar features with respect to stepped pneumatic drive line 702 and 704.

Also, even though FIG. 7 shows two separate stepped pneumatic drive lines 702 and 704 powering pneumatic surgical instrument 102, other embodiments utilize a single stepped pneumatic drive line or more than two stepped pneumatic drive lines. Thus, no limitation to the number of stepped pneumatic drive lines is implied herein to power pneumatic surgical instrument 102.

Stepped pneumatic drive line 702 has a proximal end 706 that is coupled to surgical console 100 via ports 108 and a distal end 708 that is coupled to pneumatic surgical instrument 102. Also, stepped pneumatic drive line 702 has an internal bore 710, or passageway, extending from the proximal end 706 to the distal end 708. As shown, the internal bore 710 extending through stepped pneumatic drive line 702 decreases in diameter from the end adjacent console 100 to the end adjacent pneumatic surgical instrument 102.

More specifically, as shown in FIG. 7, internal bore 710 has an inside diameter of $ID_1$ adjacent the surgical console 100 and an inside diameter of $ID_2$ adjacent the pneumatic surgical instrument 102. Inside diameter of $ID_1$ is greater than inside diameter of $ID_2$. As such internal bore 710 has it largest inside diameter of $ID_1$ adjacent the surgical console 100 and it smallest inside diameter of $ID_2$ adjacent the pneumatic surgical instrument 102.

By way of example, and not by limitation, $ID_1$ can be about 0.150 inches. Moreover, $ID_1$ can range from about 0.1 inches to about 0.3 inches. Additionally, by way of example, and not by limitation, $ID_2$ can be about 0.06 inches. Furthermore, $ID_2$ can range from about 0.01 inches to about 0.150 inches. However, other dimensions for $ID_1$ and $ID_2$ are contemplated thereby no implied limitation is set forth herein.

Accordingly, internal bore 710 is "stepped" down from the console 100 towards the pneumatic surgical instrument 102. Additionally, in this embodiment, the outside diameter of pneumatic drive line 702 remains substantially constant from the proximal end 706 to the distal end 708 of the drive line.

Based on this stepped configuration of internal bore 706, stepped pneumatic drive line 702 increases the performance of pneumatic surgical instrument 102 in comparison to other pneumatic instruments using traditional pneumatic drive line tubing. In that regard, pneumatic drive line 702 allows for a larger volume of pressurized gas to be received into the line from console 100 as compared to the size of the internal diameter of drive line adjacent pneumatic surgical instrument 102. Thus, stepped pneumatic drive line 702 allows for a larger volume of pressurized gas to be received into the line from console 100 where high flow of pressured gas is most important in order to optimize pneumatic performance.

Although FIG. 7 shows internal bore 710 having a single step down in diameter (e.g. from $ID_1$ to $ID_2$), in other embodiments it is contemplated that internal bore 702 has more than one step down. For example, internal bore 710 can have three or more different internal diameters that produce the stepped down effect. In such embodiments, the portion of bore 710 adjacent to surgical console 100 would have the largest internal diameter and each subsequent step down of bore 710 would have a smaller inside diameter. Thus, in such an alternative embodiment internal bore 710 extending through stepped pneumatic drive line 702 decreases in diameter from the end adjacent console 100 to the end adjacent pneumatic surgical instrument 102 resulting in a "stepped", "bumped", and/or "bumped tubing" drive line.

Figure 8:
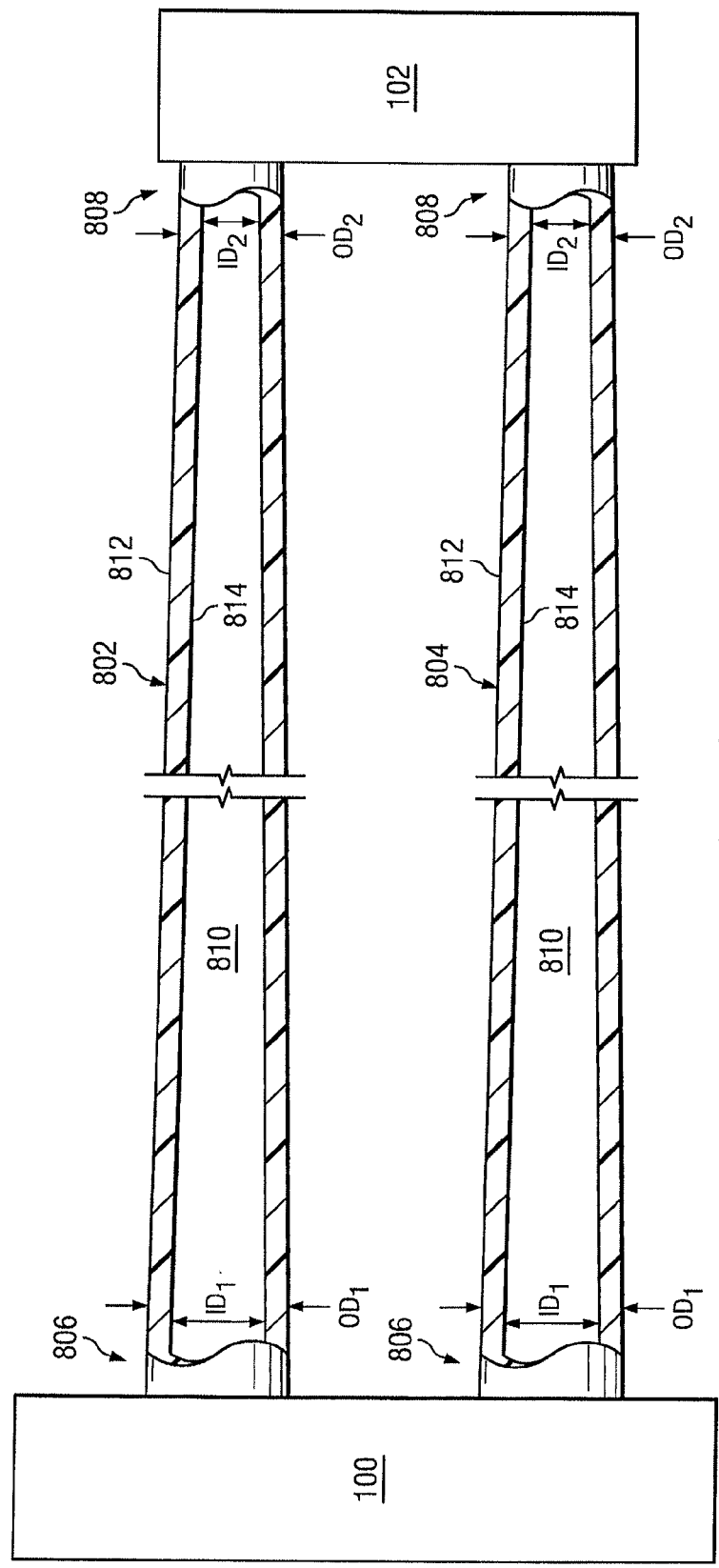
FIG. 8 is an illustration of a partial cross-sectional view of tapered pneumatic drive lines usable with the pneumatic system shown in FIG. 2 according to one aspect of the present disclosure.

FIG. 8 is an illustration of a partial cross-sectional view of tapered pneumatic drive lines usable with the pneumatic system 200. As shown, surgical console 100 and pneumatic surgical instrument 102 are coupled to tapered pneumatic drive lines 802 and 804. Tapered pneumatic drive lines 802 and 804 are used in system 200 in place of pneumatic drive lines 104 and 106, respectively. As such, all description herein related to pneumatic drive lines 104 and 106 is applicable to tapered pneumatic drive lines 802 and 804 unless stated otherwise.

Tapered pneumatic drive line 802 will be described below. The features discussed with respect to tapered pneumatic drive line 802 are present in and equally applicable to tapered pneumatic drive line 804. As such, similar reference numerals have been used in FIG. 8 to identify similar features with respect to tapered pneumatic drive line 802 and 804.

Also, even though FIG. 8 shows two separate tapered pneumatic drive lines 802 and 804 powering pneumatic surgical instrument 102, other embodiments utilize a single tapered pneumatic drive line or more than two tapered pneumatic drive lines. Thus, no limitation to the number of tapered pneumatic drive lines is implied herein to power pneumatic surgical instrument 102.

Tapered pneumatic drive line 802 has a proximal end 806 that is coupled to surgical console 100 via ports 108 and a distal end 808 that is coupled to pneumatic surgical instrument 102. Also, tapered pneumatic drive line 802 has an internal bore 810, or passageway, extending from the proximal end 806 to the distal end 808. As shown, internal bore 810 extending through tapered pneumatic drive line 802 decreases in diameter from the end adjacent console 100 to the end adjacent pneumatic surgical instrument 102.

More specifically, as shown in FIG. 8, tapered pneumatic drive line 802 continuously tapers from the surgical console 100 to the pneumatic surgical instrument 102. In other words, an exterior surface 812 of pneumatic drive line 802 and an interior surface 814 defining bore 810 both continuously taper from the proximal end 806 to the distal end 808 of tapered pneumatic drive line 802.

As such internal bore 810 has it largest inside diameter of $ID_1$ adjacent the surgical console 100 and it smallest inside diameter of $ID_2$ adjacent the pneumatic surgical instrument 102. By way of example, and not by limitation, $ID_1$ can be about 0.150 inches. Moreover, $ID_1$ can range from about 0.1 inches to about 0.3 inches. Additionally, by way of example, and not by limitation, $ID_2$ can be about 0.06 inches. Furthermore, $ID_2$ can range from about 0.01 inches to about 0.150 inches. However, other dimensions for $ID_1$ and $ID_2$ are contemplated thereby no implied limitation is set forth herein.

Moreover, tapered pneumatic drive line 802 has it largest outside diameter of $OD_1$ adjacent the surgical console 100 and it smallest outside diameter of $OD_2$ adjacent the pneumatic surgical instrument 102. By way of example, and not by limitation, $OD_1$ can be about 0.250 inches. Moreover, $OD_1$ can range from about 0.15 inches to about 0.5 inches. Additionally, by way of example, and not by limitation, $OD_2$ can be about 0.125 inches. Furthermore, $OD_2$ can range from about 0.05 inches to about 0.20 inches. However, other dimensions for $OD_1$ and $OD_2$ are contemplated thereby no implied limitation is set forth herein.

Accordingly, because tapered pneumatic drive line 802 has a non-constant inside diameter along bore 810, the tapered pneumatic drive line is optimized based on its functional needs along its length. In that regard, tapered pneumatic drive line 802 allows for a larger volume of pressurized gas to be received into the line from console 100 as compared to the size of the internal diameter of drive line adjacent pneumatic surgical instrument 102. Thus, tapered pneumatic drive line 802 allows for a larger volume of pressurized gas to be received into the line from console 100 where high flow of pressured gas is most important in order to optimize pneumatic performance. Moreover, because exterior surface 812 is tapered, tapered pneumatic drive line 802 provides a smaller drive line adjacent the pneumatic surgical instrument 102 where high flexibility and low mass are most important for a user of pneumatic surgical instrument 102. Therefore, tapered pneumatic drive line 802 is configured to provide greater flexibility and a low mass while still optimizing pneumatic performance as compared to traditional pneumatic drive lines.

Figure 9:
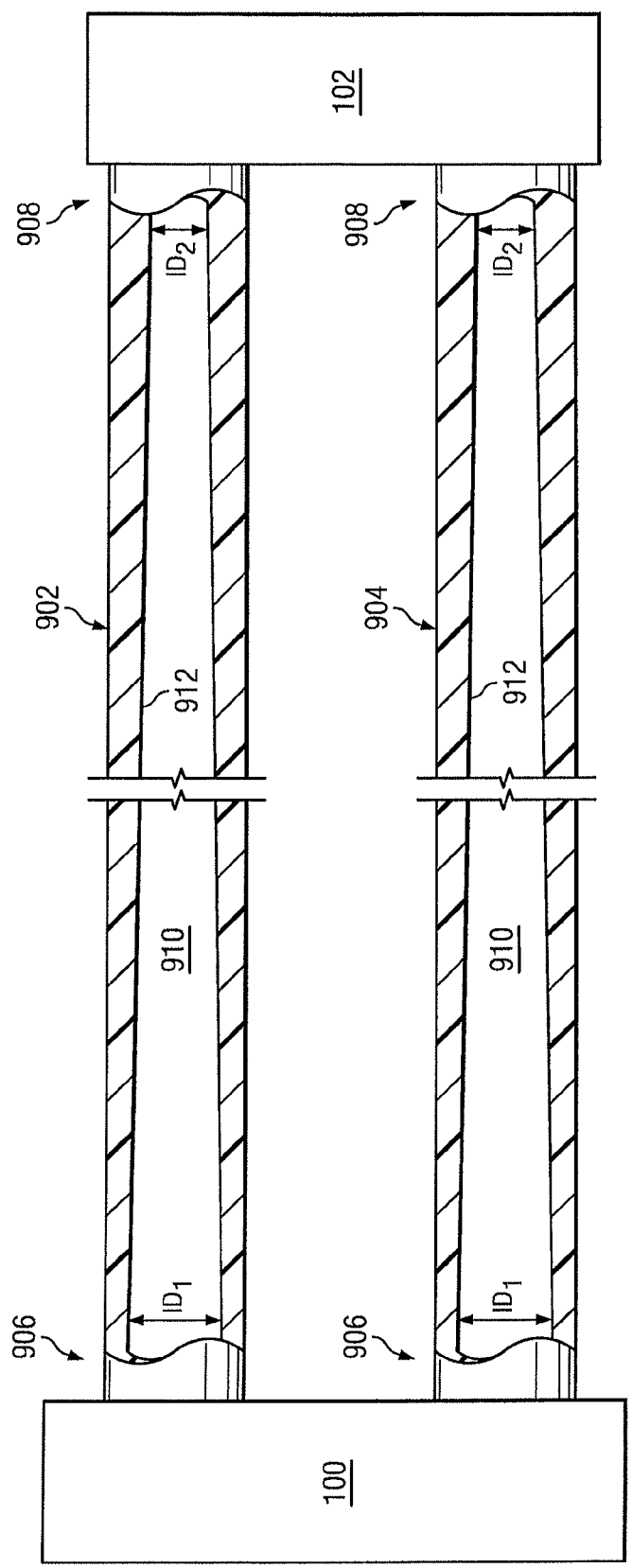
FIG. 9 is an illustration of a partial cross-sectional view of an alternative embodiment of tapered pneumatic drive lines usable with the pneumatic system shown in FIG. 2 according to one aspect of the present disclosure.

FIG. 9 is an illustration of a partial cross-sectional view of an alternative embodiment of tapered pneumatic drive lines usable with the pneumatic system 200. As shown, surgical console 100 and pneumatic surgical instrument 102 are coupled to tapered pneumatic drive lines 902 and 904. Tapered pneumatic drive lines 902 and 904 are used in system 200 in place of pneumatic drive lines 104 and 106, respectively. As such, all description herein related to pneumatic drive lines 104 and 106 is applicable to tapered pneumatic drive lines 902 and 904 unless stated otherwise.

Tapered pneumatic drive line 902 will be described below. The features discussed with respect to tapered pneumatic drive line 902 are present in and equally applicable to tapered pneumatic drive line 904. As such, similar reference numerals have been used in FIG. 9 to identify similar features with respect to tapered pneumatic drive lines 902 and 904.

Also, even though FIG. 9 shows two separate tapered pneumatic drive lines 902 and 904 powering pneumatic surgical instrument 102, other embodiments utilize a single tapered pneumatic drive line or more than two tapered pneumatic drive lines. Thus, no limitation to the number of tapered pneumatic drive lines is implied herein to power pneumatic surgical instrument 102.

Tapered pneumatic drive line 902 has a proximal end 906 that is coupled to surgical console 100 via ports 108 and a distal end 908 that is coupled to pneumatic surgical instrument 102. Also, tapered pneumatic drive line 902 has an internal bore 910, or passageway, extending from the proximal end 906 to the distal end 908. As shown, the internal bore 910 extending through pneumatic drive line 902 decreases in diameter from the end adjacent console 100 to the end adjacent pneumatic surgical instrument 102.

More specifically, as shown in FIG. 9, internal bore 910 is continuously tapered from the surgical console 100 to the pneumatic surgical instrument 102. In other words, pneumatic drive line 902 has an interior surface 912 defining bore 910 that continuously tapers from the proximal end 906 to the distal end 908 of tapered pneumatic drive line 902.

As such internal bore 910 has it largest inside diameter of $ID_1$ adjacent the surgical console 100 and it smallest inside diameter of $ID_2$ adjacent the pneumatic surgical instrument 102. By way of example, and not by limitation, $ID_1$ can be about 0.150 inches. Moreover, $ID_1$ can range from about 0.1 inches to about 0.3 inches. Additionally, by way of example, and not by limitation, $ID_2$ can be about 0.06 inches. Furthermore, $ID_2$ can range from about 0.01 inches to about 0.150 inches. However, other dimensions for $ID_1$ and $ID_2$ are contemplated thereby no implied limitation is set forth herein.

Accordingly, the internal bore 910 is continuously "tapered" down from the console 100 towards the pneumatic surgical instrument 102. However, unlike the embodiment shown in FIG. 8, the outside diameter of tapered pneumatic drive line 902 remains substantially constant from the proximal end 906 to the distal end 908 of the drive line.

Based on this tapered configuration of internal bore 910, tapered pneumatic drive line 902 increases the performance of pneumatic surgical instrument 102 in comparison to other pneumatic instruments using traditional pneumatic drive line tubing. In that regard, pneumatic drive line 902 allows for a larger volume of pressurized gas to be received into the line from console 100 as compared to the size of the internal diameter of drive line adjacent pneumatic surgical instrument 102. Thus, pneumatic drive line 902 allows for a larger volume of pressurized gas to be received into the line from console 100 where high flow of pressured gas is most important in order to optimize pneumatic performance.

Moreover, it should be noted that the pneumatic drive lines disclosed herein can be further optimized by adjusting their length. As discussed above, the pneumatic drive lines disclosed herein can be used with a surgical instrument having a probe cutter, such as probe cutter 214. It is often desirable to achieve a specified cutting rate for a cutting probe. In that regard, the length of the pneumatic drive line effects the cutting rate of a surgical instrument. Specifically, the resonance effect of the pneumatic drive line changes as the length of the drive line changes which in turn affects the cutting rate for the surgical instrument. Thus, there is a correlation between a length of the drive line and the lines ability to achieve a desired cutting rate. Accordingly, the pneumatic drive lines disclosed herein can be further optimized by having a specified length that achieves a desired cut rate.

Additionally, even though specific arrangements of pneumatic drive lines have been described herein, no limitation is implied. Thus, any combination of the pneumatic drive lines disclosed herein are useable together and/or separately to power a surgical instrument. Moreover, it is contemplated that a surgical instrument can be powered via a combination of stepped pneumatic drive lines and/or tapered pneumatic drive lines. For example, a pneumatic surgical instrument can be powered using one or more of the above described stepped pneumatic drive lines alone or in combination with one or more of the above described tapered pneumatic drive lines.

Additionally, it is contemplated that a pneumatic surgical instrument can be powered using any combination of the above described stepped pneumatic drive lines. For example, the above described stepped pneumatic drive lines can be combined in a manner to power a pneumatic surgical instrument. Thus, no limitation is implied based on the foregoing description with respect to the stepped pneumatic drive lines.

Furthermore, it is contemplated that a pneumatic surgical instrument can be powered using any combination of the above described tapered pneumatic drive lines. For example, the above described tapered pneumatic drive lines can be combined in a manner to power a pneumatic surgical instrument. Thus, no limitation is implied based on the foregoing description with respect to the tapered pneumatic drive lines.

While the present disclosure has been illustrated by the above description of embodiments, and while the embodiments have been described in some detail, it is not the intention of the applicants to restrict or in any way limit the scope of the present disclosure to such detail. Additional advantages and modifications will readily appear to those skilled in the art. Therefore, the present disclosure in its broader aspects is not limited to the specific details, representative apparatus and methods, and illustrative examples shown and described. Accordingly, departures may be made from such details without departing from the spirit or scope of the applicant's general or inventive concept.

We claim:

1. A system comprising:
    a source of compressed gas;
    a pneumatic vitrectomy probe comprising an oscillating cutter, a first chamber and a second chamber separated by a diaphragm;
    a surgical console operable to provide the compressed gas from the source of compressed gas to the pneumatic vitrectomy probe to oscillate the cutter; and
    a first flexible pneumatic drive line and a second flexible pneumatic drive line coupling the pneumatic vitrectomy probe to the surgical console, the first and second flexible pneumatic drive lines having internal bores, the surgical console configured to deliver and vent the compressed gas to and from the pneumatic vitrectomy probe through the internal bores of the first and second drive lines;
    wherein the first flexible pneumatic drive line is in fluid communication with the first chamber of the vitrectomy probe and the second flexible pneumatic drive line is in fluid communication with the second chamber of the vitrectomy probe;
    wherein a first end of the first flexible pneumatic drive line at the surgical console has a first outer diameter and a first inner diameter, wherein a second end of the first flexible pneumatic drive line at the first chamber of the vitrectomy probe has a second outer diameter that is smaller than the first outer diameter and a second inner diameter that is smaller than the first inner diameter, wherein the first flexible pneumatic drive line continuously tapers from the surgical console to the first chamber of the vitrectomy probe, and wherein the second end of the first flexible pneumatic drive line is more flexible than the first end of the first flexible pneumatic drive line;
    wherein a first end of the second flexible pneumatic drive line at the surgical console has a third outer diameter and a third inner diameter, wherein a second end of the second flexible pneumatic drive line at the second chamber of the vitrectomy probe has a fourth outer diameter that is smaller than the third outer diameter and a fourth inner diameter that is smaller than the third inner diameter, wherein the second flexible pneumatic drive line continuously tapers from the surgical console to the second chamber of the vitrectomy probe, and wherein the second end of the second flexible pneumatic drive line is more flexible than the first end of the second flexible pneumatic drive line.

2. The system of claim 1,
    wherein the first end of the first flexible pneumatic drive line is attached to a port on the surgical console and the second end of the first flexible pneumatic drive line is attached to a port on the pneumatic vitrectomy probe, and
    wherein the internal bore is tapered from the first end to the second end of the first flexible pneumatic drive line.

3. The system of claim 1, wherein the first inner diameter is within a range of 0.1 and 0.3 inches.

4. The system of claim 1, wherein the second inner diameter is within a range of 0.01 and 0.150 inches.

5. The system of claim 1, wherein the first outer diameter is within a range of 0.15 and 0.5 inches.

6. The system of claim 1, wherein the second outer diameter is within a range of 0.05 and 0.20 inches.

* * * * *

UNITED STATES PATENT AND TRADEMARK OFFICE
CERTIFICATE OF CORRECTION

| | | |
|---|---|---|
| PATENT NO. | : 10,070,990 B2 | Page 1 of 1 |
| APPLICATION NO. | : 13/314625 | |
| DATED | : September 11, 2018 | |
| INVENTOR(S) | : Brian W. McDonell | |

It is certified that error appears in the above-identified patent and that said Letters Patent is hereby corrected as shown below:

On the Title Page

Item (75), Inventors, please delete "Filip Finodeyev, Laguna Niguel, CA (US)".

Signed and Sealed this
Third Day of September, 2019

Andrei Iancu
*Director of the United States Patent and Trademark Office*